United States Patent [19]

Lee, Jr. et al.

[11] 4,001,483

[45] Jan. 4, 1977

[54] DENTAL SEALANT FOR AMALGAM RESTORATIONS

[76] Inventors: Henry L. Lee, Jr.; Jan A. Orlowski, both of P.O. Box 3836, South El Monte, Calif. 91733

[22] Filed: Oct. 22, 1974

[21] Appl. No.: 516,886

[52] U.S. Cl. .................................. 526/270; 32/15; 526/273
[51] Int. Cl.² ...................................... C08F 218/02
[58] Field of Search ............... 260/88.3 A, 86.1 E, 260/80.72, 86.1 R; 526/270, 273

[56] References Cited

UNITED STATES PATENTS

| | | | |
|---|---|---|---|
| 3,634,373 | 1/1972 | Stapleton | 260/88.3 A |
| 3,723,398 | 3/1973 | Dowbenko | 260/80.72 |
| 3,740,850 | 6/1973 | Bowen et al. | 260/86.1 E |
| 3,751,399 | 8/1973 | Lee, Jr. et al. | 260/86.1 E |
| 3,784,540 | 1/1974 | Kliment et al. | 260/86.1 E |

*Primary Examiner*—Harry Wong, Jr.
*Attorney, Agent, or Firm*—Irons and Sears

[57] ABSTRACT

Dental compositions for sealing margins between tooth structures and amalgam restorations therein, the compositions comprising (a) an alkylene glycol dimethacrylate and/or its oligomer, (b) a polymerization initiator, (c) a polymerization accelerator and (d) a secondary monomer additive; and process for sealing the margins with the compositions.

1 Claim, No Drawings

DENTAL SEALANT FOR AMALGAM RESTORATIONS

BACKGROUND

In current dental technique, a carious tooth is restored by drilling out the diseased tooth structure and replacing it with a restorative material. In most cases, this restorative is dental amalgam, a silver mercury alloy. Amalgam is plastic when newly mixed and must be placed into the cavity before it hardens. Unless applied with sufficient pressure, amalgam does not conform to the margins of the cavity satisfactorily. Amalgam also does not bond to the walls of the cavity; instead it is held in place by frictional forces. It is estimated that one half of amalgam restorations fail within ten years and the major reason for this failure is loss of marginal integrity.

An amalgam restoration can fail at the margin for a number of reasons. The amalgam itself can crack and spall away, particularly in restorations where it has been drawn out into a thin layer. Another cause is poor technique on the part of the dentist in not providing proper cavity design, or in not applying the pressure necessary to adapt the amalgam to the margin, or in trying to work with amalgam which had started to harden. Marginal failure can also occur due to thermal cycling during which the tooth structure and the amalgam do not expand at the same rate, thus causing the margin to enlarge.

The result of an enlarged margin, no matter what the cause, is seepage of saliva, oral debris, and cariogenic bacteria into the margin. In some cases a liquid becomes trapped and on warming exerts a painful pressure on the tooth structure and through it to the nerve. The impaction of food into the margin along with cariogenic bacteria produces a situation where the formation of secondary caries is almost inevitable. Thus, it is important to the preservation of amalgam restorations to be able to seal the margins to prevent seepage into them.

In the dental margin, both tooth and amalgam surfaces are of relatively high energy, but the metal surface has considerably higher critical surface tension than those of enamel and dentin. On the other hand, enamel and dentin have a critical surface tension which increases with the increase of relative humidity.

To be effective a sealant must not only manifest good penetration deep into the margins and completely seal the same, but it must manifest very good adhesion to the tooth and amalgam restoration surface. It must shrink as little as possible during cure to prevent loss of adhesion at the tooth/sealant and amalgam/sealant interfaces, and it must exhibit very good cohesive strength and resilience.

Only in this way can the sealant effectively act as a barrier to the entrance into the margin of saliva, food particles, cariogenic bacteria, and other oral debris.

Prior to the present invention, a composition exhibiting all of the above multiple desirable and salutary properties had not been found. The instant discovery provides such compositions.

INVENTION

The present invention relates to in situ polymerizable dimethacrylate compositions suitable for sealing margins between dental restorations and the opposed tooth surfaces. More particularly, the instant discovery concerns a polymerizable composition comprising (a) an alkylene glycol dimethacrylate of the formula

[hereinafter referred to as "(poly)ethylene glycol dimethacrylate"], wherein $n$ is an integer from 1 to 5, (b) a polymerization initiator, (c) a polymerization accelerator, and (d) an additive secondary monomer comprising a saturated hetero-O-cyclic ester of an acrylic acid.

All concentrations and concentration ranges herein referred to being based upon the combined weight of the components of the compositions, the initiator and accelerator are present in concentrations from about 0.5% to about 4.0% and about 0.1% to about 8.0%, respectively.

Secondary monomers contemplated herein are characterized by the fact that their structures contain a ring oxygen, such as glycidyl methacrylate, tetrahydrofurfuryl methacrylate, and other like saturated hetero-O-cyclic esters of acrylic or methacrylic acids. The concentration of additive secondary monomer is in the range of about 20% to about 70%.

According to a preferred embodiment of the present invention, a two-part formulation is formed comprising in one part (poly)ethylene glycol dimethacrylate and the initiator and in the other part (poly) ethylene glycol dimethacrylate, the accelerator and the additive secondary monomer.

Alternatively, all of the poly (ethylene) glycol dimethacrylate may appear in the initiator part or the accelerator part; likewise, the additive secondary monomer may appear in either part or in both parts.

It is advantageous to include in the formulations a minor amount, e.g., less than 1%, of a fluorescent agent, such as thiophene bis(benzoxazolyl), 3-phenyl-7-triazinylamino coumarin, stilbene naphthotriazole, and benzotriazole phenyl coumarin. When a two-part formulation is employed, the fluorescent agent may appear in either part thereof or in both parts.

According to still another embodiment a hydroxyalkyl ($C_1 - C_5$)-methacrylate and/or a hydroxyalkyl ($C_1 - C_5$) acrylate may be present in the formulation, preferably in the accelerator part when a two-part formulation is prepared, in a concentration up to about 35%, preferably less than about 20%. It has been found that adhesion to wet surfaces is significantly increased when this additive is present in the just-mentioned concentrations.

Pursuant to the present invention, the components are mixed and polymerized in situ. In the case of a two-part formulation, blending may be effected by placing either simultaneously or consecutively a drop of each into the margin being sealed. The resulting blend sets or cures in about two (2) minutes at room temperature. Of course, both drops (formulations) may be pre-blended immediately before introduction into the margin.

If desired, all components may individually be brought together and thoroughly admixed just prior to introduction into the margin. As is evident, three-part formulations or other multiple-part formulations are herein contemplated, with the proviso that an initiator/accelerator/monomer combination be avoided until just prior to or upon filling the margin.

It has been found, according to the instant discovery, that the above compositions quite surprisingly overcome the significant and different surface tensions possessed by the opposed surfaces of the tooth and amalgam and readily penetrate into the margin.

The (poly)ethylene glycol dimethacrylates herein contemplated have a viscosity below about 10 centipoises and surface tensions between about 38 and about 39 dynes/centimeter. According to still another embodiment, it has been found that blending or mixing of the preferred two-part formulations may be accelerated by differentiating the density of the components, e.g., by using a different blend of monomers in each part or a low viscosity but high boiling solvent, preferably of the halogenated hydrocarbon type.

Typical accelerators or promoters within the purview of the present invention are the tertiary amines, including but not limited to N,N-di(lower)alkyl-p-toluidines (e.g., N,N-dimethyl-p-toluidine and N,N-diethyl-p-toluidine) and N,N-di(lower)alkyl anilines, such as N,N-dimethyl aniline and N,N-diethyl aniline.

The preferred initiators or catalysts are the free-radical catalysts, such as the organic peroxides and particularly benzoyl peroxide and lauroyl peroxide.

If desired, a conventional inhibitor may be present in minor amounts, such as in one or both parts of the preferred two-part formulations. A typical inhibitor for, say, a dimethacrylate/initiator part is 2-tertiary-butyl-4-hydroxytoluene, and for say, a dimethacrylate/accelerator part is hydroquinone. Less than about 3% inhibitor is herein contemplated.

EXAMPLES

The present invention will be more fully described by reference to the following examples which illustrate certain preferred embodiments of the present invention.

EXAMPLE I

| Example I Part A | Percent by Weight |
|---|---|
| diethylene glycol dimethacrylate | 96.40 |
| benzoyl peroxide | 3.00 |
| 2-t-butyl-4-hydroxytoluene | 0.06 |
| Part B | |
| diethylene glycol dimethacrylate | 49.35 |
| glycidyl methacrylate | 49.35 |
| N,N-bis-hydroxyethyl-p-toluidine | 1.20 |
| UV fluorescent agent, Tinopal PCR* | 0.10 |

An equal number of drops of Part A and B is applied with syringes on the margin of amalgam restorations. The resulting blend sets in 2 minutes at room temperature. Cured material shows good adaptation to both amalgam and tooth walls when tested on teeth extracted four weeks after application as well as in tests performed in vivo after thermocycling (500 fast temperature changes in the range of 0 60° C). The physical properties of the cured material are as follows:

| | |
|---|---|
| Compressive strength | 20,000 psi |
| Diametral tensile strength | 3,000 psi |
| Hardness, Shore D | 75 |
| Water sorption | 3.9% |
| Contact angle of an uncured Part A and B is: | |
| on enamel conditioned with 50% H₃PO₄ | <1° |
| on amalgam | 5° |

EXAMPLE II

| Example II Part A | Percent by Weight |
|---|---|
| diethylene glycol dimethacrylate | 96.94 |
| benzoyl peroxide | 3 |
| 2-t-butyl-4-hydroxytoluene | 0.06 |
| Part B | |
| triethylene glycol dimethacrylate | 28.5 |
| tetrahydrofurfuryl methacrylate | 68.5 |
| N,N-bis(hydroxyethyl)-1-toluidine (accelerator) | 3 |

The material sets in 130 seconds at room temperature at 23° C.

| Properties of cured material: | |
|---|---|
| Compressive strength | 20,000 psi |
| Diametral tensile strength | 3,100 psi |
| Hardness, Shore D | 76 |
| Water Sorption | 3.5% |
| Contact angle of an uncured Part A and B is: | |
| on conditioned enamel | <1° |
| on amalgam | <5° |

The material shows good adaptation to both tooth structure and amalgam when used in the test described in Example I, supra.

EXAMPLE III

| Example III Part A | Percent by Weight |
|---|---|
| triethylene glycol dimethacrylate | 58.64 |
| glycidyl methacrylate | 38.64 |
| benzoyl peroxide | 5 |
| 2-t-butyl-4-hydroxytoluene | 0.05 |
| Part B | |
| tetraethylene glycol dimethacrylate | 77.95 |
| hydroxyethylmethacrylate | 17.95 |
| dimethyl-p-toluidine | 4 |
| hydroquinone | 0.1 |

The material sets in 140 seconds at room temperature of 23° C.

| Properties of cured material: | |
|---|---|
| Compressive strength | 20,000 psi |
| Diametral tensile strength | 3,000 psi |
| Hardness, Shore D | 78 |
| Contact angle of an uncured Part A and B is: | |
| on conditioned enamel | <1° |
| on amalgam | <5° |

The material shows good adaptation to both tooth structure and amalgam when used in a test described in Example I, above.

Pursuant to statutory requirements there are described above the invention and what are now considered its best embodiments. It should be understood, however, that the invention can be practiced otherwise than as specifically described, within the scope of the appended claims.

What is claimed is:

1. A composition for use as a dental sealant, for sealing the dental margin between a tooth structure and an amalgam restoration, that is characterized by good ability to penetrate a space between the tooth structure and the amalgam restoration, and that is packaged in two separate packages, each of which remains in its curable state as packaged but that upon mixing one with the other upon application to a dental margin, cures in about two minutes at room temperature, and that as mixed comprises a curable composition of:

a. an alkylene glycol dimethacrylate of the formula

wherein $n$ is an integer from 2 to 4, inclusive;
b. a polymerization initiator;
c. a polymerization accelerator; and
d. an additive secondary monomer selected from the group consisting of
glycidyl methacrylate and
tetrahydrofurfuryl methacrylate, in the concentration from about twenty percent to about seventy percent based upon total weight of the composition, the (b) and (c) components being present in minor, effective amounts, and the balance of the composition being essentially the dimethacrylate.

* * * * *